United States Patent
Winchester, Jr. et al.

(10) Patent No.: US 7,826,890 B1
(45) Date of Patent: Nov. 2, 2010

(54) OPTICAL DETECTION OF INTRAVENOUS INFILTRATION

(75) Inventors: Leonard W. Winchester, Jr., Yorktown, VA (US); Nee-Yin Chou, Yorktown, VA (US)

(73) Assignee: WinTec, LLC, Yorktown, VA (US)

( * ) Notice: Subject to any disclaimer, the term of this patent is extended or adjusted under 35 U.S.C. 154(b) by 971 days.

(21) Appl. No.: 11/295,215

(22) Filed: Dec. 6, 2005

(51) Int. Cl.
*A61B 6/00* (2006.01)
*A61B 5/05* (2006.01)

(52) U.S. Cl. ............... 600/477; 600/407; 600/473; 600/476; 600/547

(58) Field of Classification Search ............ 600/407, 600/431, 437, 547, 587, 473, 476, 477
See application file for complete search history.

(56) References Cited

U.S. PATENT DOCUMENTS

| | | | |
|---|---|---|---|
| 4,877,034 A | | 10/1989 | Atkins et al. |
| 6,487,428 B1 | | 11/2002 | Culver et al. |
| 6,758,845 B1 | * | 7/2004 | Weckwerth et al. ............ 606/9 |
| 7,047,058 B1 | * | 5/2006 | Dvorsky et al. ............. 600/407 |
| 7,122,012 B2 | * | 10/2006 | Bouton et al. ............... 600/587 |
| 7,184,820 B2 | * | 2/2007 | Jersey-Willuhn et al. .... 600/547 |
| 7,546,776 B2 | * | 6/2009 | Ono ........................ 73/861.25 |

* cited by examiner

*Primary Examiner*—Max Hindenburg
*Assistant Examiner*—Adam J Eiseman
(74) *Attorney, Agent, or Firm*—James Creighton Wray; Meera P. Narasimhan

(57) ABSTRACT

An intravenous infiltration detection apparatus for monitoring intravenous failures, which applies an optical method coupled with fiber optics and algorithms for tissue optics to provide a means for noninvasive detection of intravenous infiltration surround the site of IV injection. In the invention, the tissue surrounding the injection site is exposed to a single-wavelength of electromagnetic radiation, and light is collected with only one detector. Changes in the relative intensity of the radiation reflected, scattered, diffused or otherwise emitted provide a means for monitoring infiltration. The invention provides routine, automated, continuous, and real-time monitoring for patients undergoing IV therapy.

34 Claims, 9 Drawing Sheets

OPTICAL DETECTION OF INTRAVENOUS INFILTRATION

BACKGROUND OF THE INVENTION

In the United States, approximately 80% of hospital patients require intravenous (IV) therapy and approximately 50% of the IV lines fail due to infiltration, a clot in the cannula, an inflammatory response of the vein, or separation of the cannula from the vein. IV infiltration is usually accompanied by pain, erythema, and/or swelling at the cannula tip or the insertion site. Severe infiltration may lead to necrosis requiring skin debridement, skin grafting, or amputation. One common area of malpractice lawsuits filed against physicians and nurses involves infiltration. The leakage of cytotoxic drugs, intravenous nutrition, solutions of calcium, potassium, and bicarbonate, and even 10% dextrose outside the vein into which they are delivered is known to cause tissue necrosis and to precipitate significant scarring around joints. An infiltration rate of 0.1-1% has been reported in cases where contrast agents were used in medical imaging procedures. Early detection of infiltration prevents the occurrence of serious incidents that may require surgical correction.

It has been postulated that there are six predictors of infiltration—catheter material, age of patients, anatomic insertion site, hyperalimentation, the use of furosemide, and the use of dopamine. The age of patient is a very important factor for the risk of infiltration. Because the amount of connective tissue is limited in elderly patients as well as the very young, they are prone to extensive diffusion of infiltrated fluid. The patient's osmotic balance is another important consideration. Obese patients or patients with low albumin or edema may not have normal tissue responses to pressure.

Infiltration may develop in different ways: (a) the steel needle or plastic cannula may pierce the wall of the vein, allowing fluid to flow into the interstitial space; (b) a clot distal to the cannula may develop, causing narrowing of the vein wall, blocking blood flow, increasing backpressure, and infiltration at the needle insertion site; (c) certain IV fluids may cause change in blood pH and constriction of veins with increasing pressure and subsequent infiltration; (d) the IV cannula or the infused solution may cause an inflammatory reaction, increasing permeability of the vein and allowing fluid to leak into surrounding tissues; and (e) the cannula may be dislodged from the vein. The extent of tissue damage caused by infiltration depends on the drug, the dosage, the site of IV administration, and the exposure duration. Injuries due to infiltration of cytotoxic drug infusions range from 0.1-0.7%. Severe infiltration injuries often require surgical treatment and even amputation. One study reported that infiltration results in skin loss in 0.24% of the peripheral lines.

There are several methods currently existing for detecting infiltration: visual and tactile examinations; monitoring IV line pressure; checking for blood return; and electromagnetic radiation detection.

Visual and tactile examinations of IV sites are the most widely used methods for detecting infiltrations. The infiltrated site may appear swollen or puffy. In this case erythema may also be present. Infiltrations may also appear as a pale area where the infiltrate has pooled below the skin. The skin may feel cooler than the surrounding area due to rapid entrance of the IV fluid into the tissue before it can be warmed to body temperature. The visual and tactile examination technique is ineffective in detecting infiltration, since by the time infiltration is detected, tissue damage has already occurred.

IVs are administered either by gravity control or infusion pumps. For gravity control, the solution head height, defined as the vertical distance from the fluid meniscus to the IV site, generates the pressure necessary to infuse IV fluid. In theory, gravity control would stop fluid infusion when sufficient fluid accumulates in the interstitial space. Once the fluid flow stops, an alarm alerts the nurse to check the IV site. For gravity control IV, the solution reservoir can be lowered to below IV sites. If blood flows toward the lowered reservoir, infiltration is less likely to occur. However, this technique cannot reliably detect infiltration.

Infusion pumps provide volumetric and timed delivery of IV fluids under conditions of increased resistance to flow. The occlusion pressure can be as high as 25 psi (1293 mm Hg). The disadvantage of maintaining a high pressure is that a potential hazard to patients exists should infiltration occur. Studies of the performance of low, non-variable pressure infusion pumps in alerting the nurses to infiltrations, show that while 64% of IV sites show clinical evidence of infiltration, no alarm occurs. It has been reported that infiltration may be detected by monitoring the IV pressure, one measures either the in-line IV pressure or the in-line IV pressure dissipation after a brief pressure increase. However, both pressure monitoring methods have proven unreliable, since there is limited predictability of change in in-line pressure following infiltration. Perfusion, diffusion, and metabolic processes occurring in living tissue and intra- and inter-patient differences render the use of pressure monitoring for infiltration detection ineffective.

Another method of checking for infiltration is to look for a blood return. Removing the positive pressure caused by the infusion controller (either gravity or infusion pump) checks for the presence of a blood return. While the lack of a blood return indicates infiltration, the presence of a blood return cannot be construed as the absence of an infiltration.

One commercial device, the Venoscope® uses transillumination to locate the patient's peripheral venous network. It employs two movable optical fibers to illuminate the skin. The veins appear as dark areas beneath the skin. Detection of veins is by visual inspections. The Venoscope® must be used in a dimly lit room in order to have sufficient contrast to locate the venous network. It has been claimed that the Venoscope® can be used to detect IV infiltration. However, the detection is performed by subjective visual inspections.

Another method of detecting infiltration is described in U.S. Pat. No. 4,877,034 (Atkins). The Atkins invention teaches an IV monitoring technique that allows detection of tissue infiltration by exposing tissue surrounding the site of intravenous injection to a plurality of wavelengths of electromagnetic radiation. Changes in the relative levels of the detected radiation at each wavelength as compared to a baseline reading obtained when no infiltration is occurring indicate tissue infiltration. Electromagnetic radiation sources of at least two different wavelengths of radiation are used to direct electromagnetic radiation at the tissue surrounding the intravenous insertion site. The amount of radiation reflected, scattered and absorbed under certain conditions depends on the wavelength of the electromagnetic radiation and local tissue properties. The intensities of the detected radiation at the two wavelengths change when infiltration occurs, and these changes are different for different wavelengths. That is, infiltration affects the intensity of the detected electromagnetic radiation at one wavelength more than that of the second wavelength, allowing the difference to be used to indicate infiltration. While Atkins teaches a noninvasive method of detecting tissue infiltration, it is unnecessarily complex.

U.S. Pat. No. 6,487,428 (Culver) describes an IV monitoring apparatus for detecting IV infiltration by monitoring light transmitted through the tissue of the patient in proximity to a site at which fluid is being injected. Light is irradiated from a plurality of light sources in an encoded manner into the body part at the site at which the fluid is injected and the light that is reflected, scattered, diffused or otherwise emitted from the body part is detected individually by a plurality of light detectors. Signals representative of the detected light are collected and, prior to injection of the fluid, references are developed against which measurements made during injection of the fluid are compared. Like Atkins, the Culver invention is unnecessarily complex.

To solve the shortcomings in the existing systems, a need exists for a simple, reliable, inexpensive, and noninvasive method of monitoring IV sites for early detection of infiltration.

SUMMARY OF THE INVENTION

The present invention solves the shortcomings of existing systems by providing a device and method:
(1) That is potentially sensitive and robust against false alarms. Using the present invention on simulated infiltrations, the minimally detectable fluid volume is about 0.1 ml when a syringe is used to inject the fluid and it is about 0.02 ml when either a syringe pump or an infusion pump is used to infuse the fluid. The sensitivity, specificity, positive and negative predictive values of the present invention are calculated to be 97%.
(2) That monitors both the insertion site and any infiltration that may occur without direct attention of medical personnel, providing continuous monitoring of the IV site.
(3) That eliminates the subjectivity of observer-based visual inspections. It applies optical technology as compared with pressure monitoring using infusion pumps.
(4) That may be incorporated into existing IV systems to provide an alarm signal to alert the patient and/or healthcare personnel of potential infiltrations.
(5) That can detect small amounts of infiltrate well before a skilled observer detects the infiltration.
(6) That uses a single light source and a single detector making the present invention less complex and more reliable than any prior art devices.

An intravenous infiltration detection apparatus according to the present invention includes a light source, a power supply, two light guides, a detector, an electronics unit, a skin-contact sensor, and an indicator. The power supply provides power to the light source, the detector, the electronics unit, and the indicator. The light source provides illumination to the infusion site. The first light guide delivers incident electromagnetic radiation to the infusion site, its proximal end is optically coupled to the light source and its distal end is embedded in a skin-contact sensor placed near the IV infusion site of a patient. The second light guide collects the electromagnetic radiation reflected, scattered, diffused or otherwise emitted from the tissue near the infusion site and delivers the collected radiation to the detector. The proximal end of the second light guide is optically coupled to the detector and, like the first light guide, its distal end is embedded in the skin-contact sensor. The distal ends of both the illumination (first) light guide and the collection (second) light guide are flush with the skin-contact side of the skin-contact sensor. The distance between the distal ends of the two light guides in the skin-contact sensor is approximately a few millimeters. The skin-contact sensor can be made of different materials, including, but not limited to, wood and plastics. The skin-contact sensor is attached to the skin via a securing device such as, but not limited to, a piece of surgical tape. A detector at the proximal end of the second light guide receives the collected electromagnetic radiation from the tissue. An electronics unit connected to the detector analyzes the collected radiation. The information on the occurrence of IV infiltration is exhibited on the indicator. In one example of the present invention, the indicator may display normal infusion (no infiltration), possible infiltration, and infiltration.

The electronics unit further comprises (a) a power module enclosing a power source, (b) a driver module for regulating the light source, (c) a detector module for adjusting the gain and offset of the detector, receiving signals from the photodetector, and sending the received signals to an analyzer module, (d) an analyzer module for analyzing the received signals, and (e) an indicator module for triggering the alarms.

The present invention is also directed toward a method of monitoring tissue infusion site for the detection of infiltration during IV infusion. The method comprises means for controlling the intensity of the light source; means for directing light onto tissue near an IV site; means for collecting light from the tissue near the IV site; means for delivering the collected light to a photon detection device; means for developing, prior to injection of the IV fluid, baseline signals associated with the light source and light detector and against which measurements made during the injection of IV fluid are compared; means for comparing signals collected during IV injection/infusion with the associated baseline signals, means for determining the alarm levels, means for triggering the alarms, and means for indicating the alarms.

These and further and other objects and features of the invention are apparent in the disclosure, which includes the above and ongoing written specification, with the claims and the drawings.

DETAILED DESCRIPTION OF THE PREFERRED EMBODIMENTS

Figure 1:
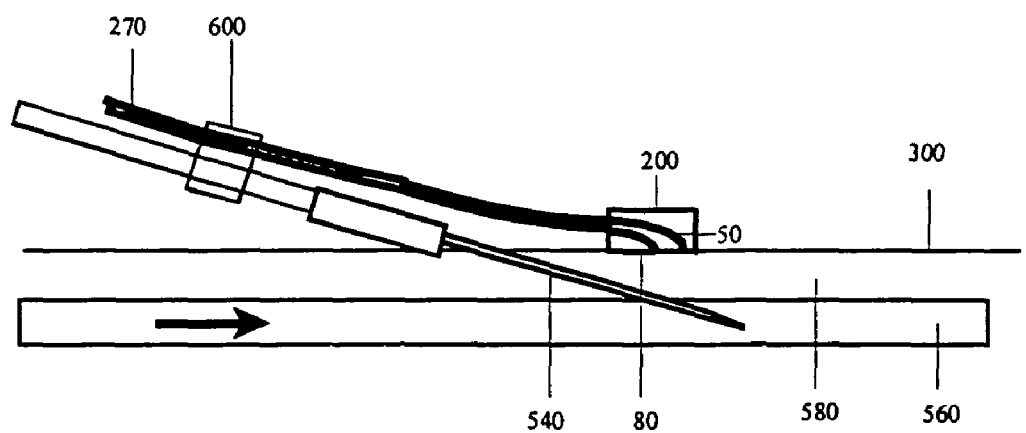
FIG. 1 is a schematic diagram depicting the insertion of the needle into a vein and the placement of a skin-contact sensor on the skin.

As shown in FIG. 1, when a beam of optical radiation impinges on skin 300 near an IV infusion site, the radiation reflected, scattered, diffused or otherwise emitted from the skin can be measured. As shown in the figure, an optical fiber bundle 270 comprises an illumination light guide 50 that provides illumination to the infusion site and a collection light guide 80 that collects the electromagnetic radiation reflected from the infusion site. The ends of the light guides 50 and 80 are embedded in a skin-contact sensor 200 that is secured onto the skin 300. A needle 540 is inserted through the skin 300 into a vein 560 for infusion of IV fluids.

When IV fluid infiltrates the interstitial tissue space, optical density of tissue changes. This change can be measured as follows. First, the infusion site is illuminated using a beam of electromagnetic radiation with certain wavelength. Before energizing the illumination source, the radiation collected after insertion of the needle 540 establishes an ambient signal which is continuously monitored and recorded to provide a running ambient signal value, and this value is subtracted from subsequent radiation values collected when the illumination source is energized. In a preferred embodiment of the invention, a light-emitting diode (LED) is employed as the illumination source. The LED can be controlled to operate in a predefined on-off mode. For example, it can be energized for a predefined duration such as 1 s, de-energized and stay so for a predefined duration such as 4 s, and re-energized again. When the illumination source is energized, the optical signals are again collected from the infusion site, recorded, and averaged to establish a baseline $R_0$. During IV infusion, optical signals (R) are continuously collected at predefined intervals. The R values are averaged over a predefined duration to minimize the effects of motion artifacts caused by the patient's movements and/or the action of tactile examination.

When an IV fails and the IV fluid infiltrates the interstitial space, the values of the collected signals from the infusion site change considerably. In one embodiment of the invention, this change is used to infer the presence of infiltrated fluid in subcutaneous tissue 580 using the expression:

$$F = 1 - R/R_0 \qquad \text{Equation 1}$$

The fractional change F is continuously recalculated. The present invention provides a means to interpret the conditions of infusion such as normal infusion, potential infiltration, and definitive infiltration, from the value of F. A suitable choice of F can be used as the alarm threshold for setting a trigger signal to an alarm. The use of the relative change in the collected radiations from infusion site minimizes the effects caused by patients with different skin color, shade, and/or texture. The time required to detect IV infiltration depends on factors such as the infusion rate, diffusivity of tissue, osmotic properties of the infused fluid, and the location of the skin-contact sensor 200 relative to the infusion site.

Referring to FIG. 1, the optical fiber bundle 270 is attached to the IV line via a securing mechanism, such as a clamp 600, and the location of the clamp 600 is chosen such that it allows easy attachment of a skin-contact sensor 200 to the IV infusion site on the skin 300 via a securing mechanism, such as surgical tapes. The skin-contact sensor 200 is secured onto the skin 300 near the intravenous insertion site.

The selection of the operating wavelength of the illumination source depends on several factors such as the photon penetration depth, the available light sources and detectors, and the absorptions of tissue. The photon penetration depth, defined as the distance at which the intensity of radiation is reduced to 1/e of its initial value, is smaller for shorter wavelength radiations. In one embodiment of the invention, LEDs with a wavelength of 850 nm are the preferred light source. The 850 nm LEDs have a deep photon penetration depth (approximately 1.3 mm) and high intensity, suitable detectors are readily available, and at this wavelength, plastic optical fibers have acceptable transmission, and water and common chromophores have low absorptions.

The present invention provides a method for determining the optimal wavelengths for an intravenous infiltration detection apparatus. The method includes means for conducting simulated infiltrations by injecting subcutaneously IV fluids into tissue, means for illuminating the infusion site with only a one-wavelength light source, means for sequentially and separately energizing the single, one-wavelength light source, means for collecting radiations reflected, scattered, diffused or otherwise emitted from the infusion site with only one light source energized, means for bundling multiple illumination fibers and collection fibers, and means for analyzing the collected radiations.

Figure 2:
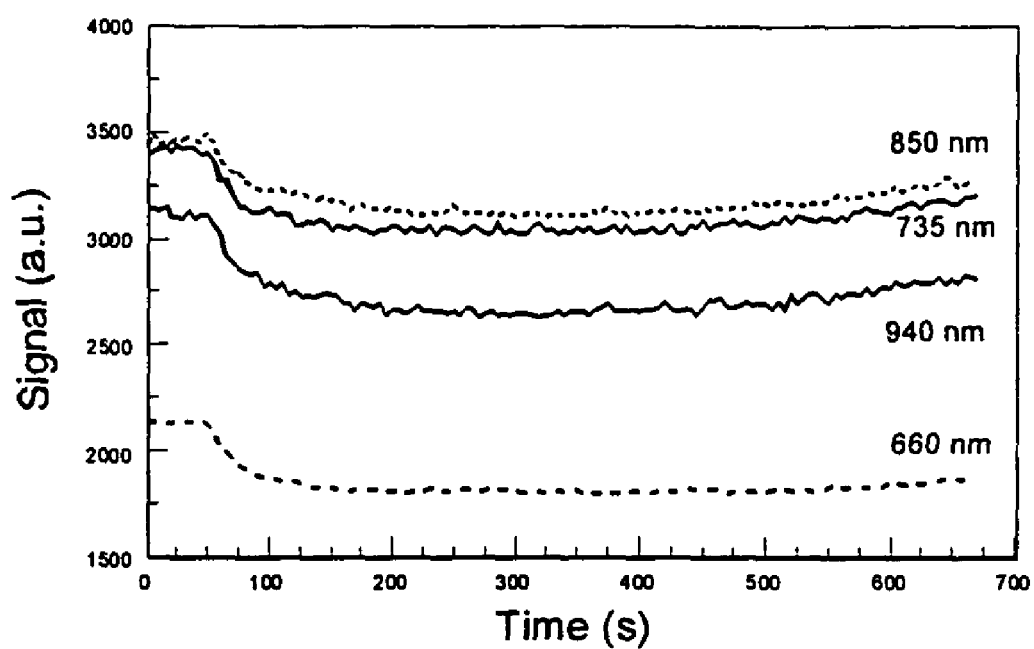
FIG. 2 is a diagram showing the collected optical signals from a skin surface at four different wavelengths as a function of time.

FIG. 2 shows an example of a graph developed to assist in the wavelength selection process, depicting the radiations collected near the infusion site from the skin using four different light sources emitting 660, 735, 850, and 940 nm wavelength radiations as a function of infusion time. The data shown in FIG. 2 are obtained with a 5-fiber skin-contact sensor consisting of one collection fiber coupled to a photon detection device and four illumination fibers coupled to four different light sources such as the LEDs. The intensity of the 660 nm LED is about 70% of the other three LEDs. The flow rate of the IV fluid injected into tissue is controlled with an infusion pump. Referring to FIG. 2, at T=50 s, the infusion pump is turned on and IV fluid is pumped into tissue at a rate of 10 ml/hr. The decrease in the collected signals R can be clearly seen at all four wavelengths. At T=400 s, a minor weal starts to form, resulting a gradual increase of R. The pump is stopped at T=528 s. As clearly shown in FIG. 2, the near-infrared LED (850 nm) provides the highest signals.

Another important factor affecting the wavelength selection is the effect of antiseptics on the signal strengths of collected radiation from the injection site. Isopropyl alcohol and betadine (povidone-iodine) are commonly used to cleanse the injection site. The effect of these antiseptics is investigated by measuring the collected radiation from the injection site as a function of wavelength for (a) untreated injection site, (b) injection site treated with isopropyl alcohol, (c) injection site treated with betadine and followed with alcohol, and (d) injection site treated with betadine and allowing the skin to dry.

Figure 3:
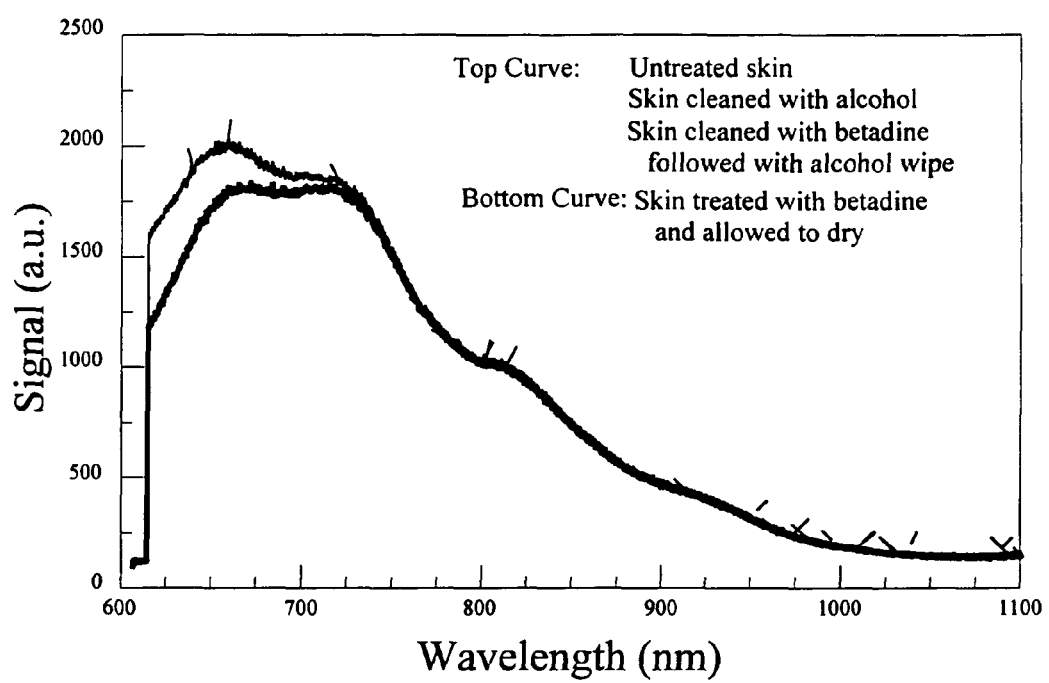
FIG. 3 is a graph showing the effect of antiseptics on the collected optical signals from skin as a function of wavelength.

FIG. 3 shows an example of the graph depicting the relative intensities of radiations collected from a sampling site on the skin for the above-described conditions as a function of wavelength, using a broadband light source for illuminating the skin. As shown in FIG. 3, the measurements on the skin for the fourth condition (d) (shown as the lower curve) show weaker signals below 720 nm than the measurements for the other three conditions, due to the absorption of Betadine at shorter wavelength, whereas the signals for the first three conditions (a-c) are indistinguishable (shown as the upper curve), indicating that alcohol has negligible effect on the collected signals and it wipes out the effect of betadine, and most importantly, for wavelengths longer than around 720 nm, there shows no effect of the commonly used antiseptics on the collected signals. In a preferred embodiment of the invention, a single LED emitting at around 850 nm is selected as the light source. The 850 nm radiation is especially effective in humans, since the absorptions of melanin and water are relatively low at that wavelength. Melanin is the dominant absorber in the epidermis of human skin; the absorption coefficient of melanin is highest in the UV spectral region (200-400 nm) and falls exponentially for wavelengths greater than 400 nm.

The present invention also provides a method for determining the number of wavelengths required for an intravenous infiltration detection apparatus. The method includes means for conducting induced infiltrations by injecting IV fluids into a vein and inducing the infiltration by either pushing the injection needle through the vein or by pulling the needle out of the vein.

Figure 4:
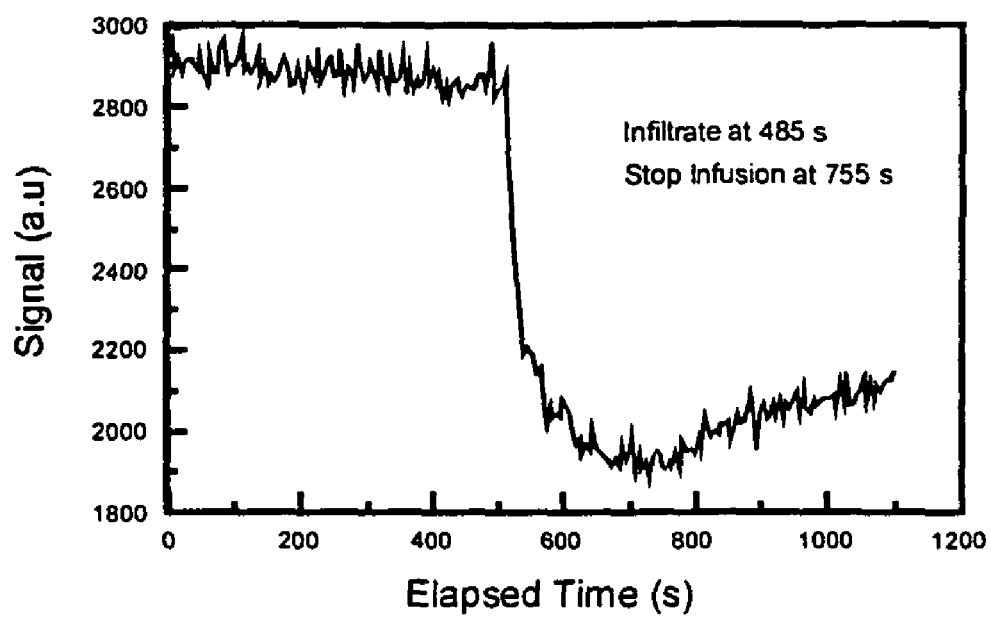
FIG. 4 is a graph showing the collected optical signals from skin as a function of time for an infiltration occurring at about 510 s.

FIG. 4 shows an example of the graph depicting the signals collected near the injection site as a function of time at a single wavelength. As shown in FIG. 4, the infusion starts at T=0 s (in this example, it is 7 min after the needle was inserted into the vein). At T=485 s, an induced infiltration is initiated. A 10% decrease in R is observed over a period of 20 s. At T=755 s, infusion is stopped and the signal begins to increase gradually. The occurrence of infiltration is clearly seen in FIG. 4. Light sources with different wavelengths are used and the results compared. One very important aspect of the invention is that unlike prior arts, only one wavelength from one light source is needed to accurately detect IV infiltration.

Figure 5:
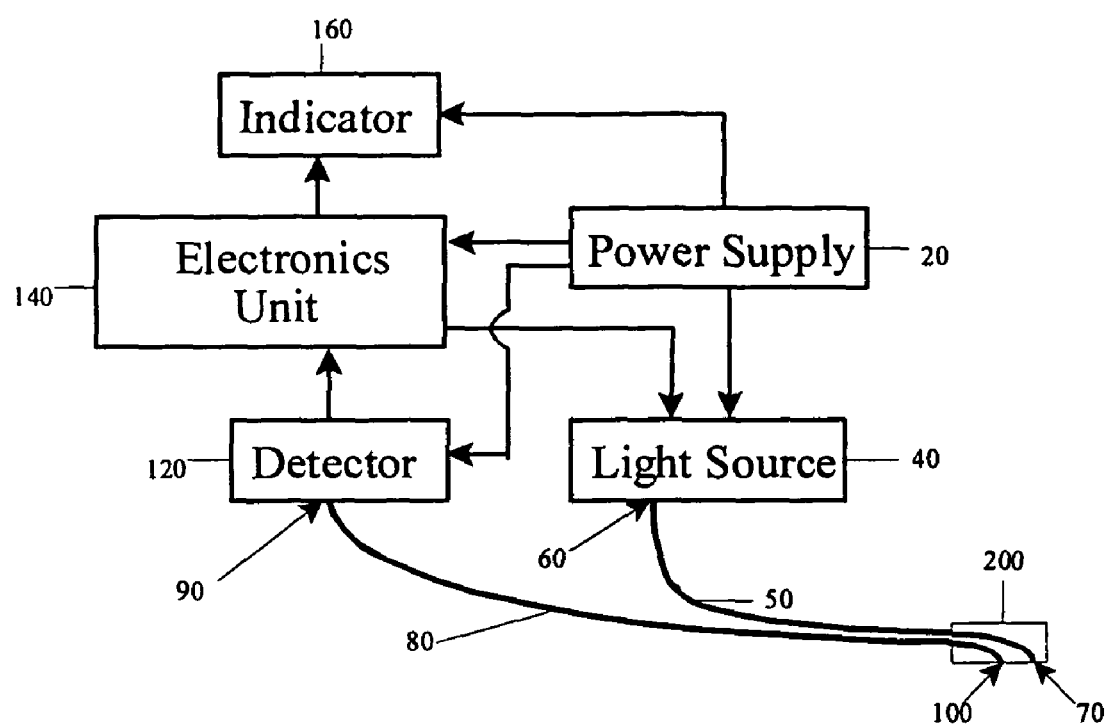
FIG. 5 is a schematic block diagram of the optical infiltration detection apparatus of the present invention.

FIG. 5 is a schematic diagram of a preferred embodiment of the invention. The optical IV infiltration detection apparatus utilizes a power supply 20, which may be any power supply known to those of average skill in the art. The power supply 20 is connected to an electromagnetic radiation source 40. In a preferred embodiment of the invention, the electromagnetic radiation source 40 is a light-emitting diode (LED). An LED with a wavelength of 850 nm has been found effective due to its deep photon penetration depth, high intensity, acceptable transmission of plastic optical fibers at this wavelength, and the availability and suitability of the LEDs and detectors. Additionally, water and common chromophores have low absorptions at 850 nm. A first light guide 50, which contains an optical fiber or multiple fibers, has a proximal end 60, which is optically coupled, to the light source 40 via a connector, such as an SMA connector. The incident electromagnetic radiation is delivered from the light source 40 through the light guide 50 to a distal end 70 of the same light guide. The first light guide 50 provides illumination to the infusion site. The distal end 70 of the first light guide 50 is embedded in a skin-contact sensor 200 that is mounted near the IV infusion site of a patient. A second light guide 80 which contains an optical fiber or multiple fibers is used to collect the electromagnetic radiation reflected, scattered, diffused or otherwise emitted from the infusion site and deliver the collected radiation to a light detection device 120. A distal end 100 of the second light guide 80 is also embedded in the skin-contact sensor 200. In a preferred embodiment of the present invention, the light detection device 120 is a GaAlAs photodiode encased in a TO-5 housing, with a 5-mm$^2$ sensing area. The GaAlAs photodiodes have good gain and low noise. An electronics unit 140 receives the detected signals from the light detection device 120 and analyzes the detected signals, stores the analyzed signals, and sends the analyzed results to an indicator (alarm) device 160. The indicator device 160 triggers an alarm signal when the analyzed results reach a certain level. The alarm signals such as audible signals, flashing lights, signals displayed on monitors in the nurses' stations provide warnings to medical staffs of potential occurrence of IV failures. A proximal end 90 of the second (collection) light guide 80 is connected to the detector via a connector such as an SMA connector. Both ends of the light guides are polished with polishing laps, ending with a 0.1 μm lap.

In a preferred embodiment of the invention, the light guides 50 and 80 are jacketless plastic optical fibers made of polymethyl methacrylate (PMMA), with a 500 μm core diameter. In the visible region, plastic optical fibers have about 10-15% lower transmission than glass fibers. At the near-infrared (NIR) region, plastic fibers have moderate attenuation. However, since the fiber lengths are 2-m or less, the loss in transmission is immaterial. Plastic fibers are more flexible and cost less than glass fibers.

In one embodiment of the invention, the first and second light guides, 50 and 80, each contains a single optical fiber and the distal ends, 70 and 100, of these fibers are embedded in a skin-contact sensor 200 for attachment to the skin of the patient. In an alternate embodiment of the invention, the first light guide 50 is a single optical fiber and the second light guide 80 comprises multiple optical fibers having multiple distal ends spaced around the distal end 70 of the first light guide 50.

Figure 6:
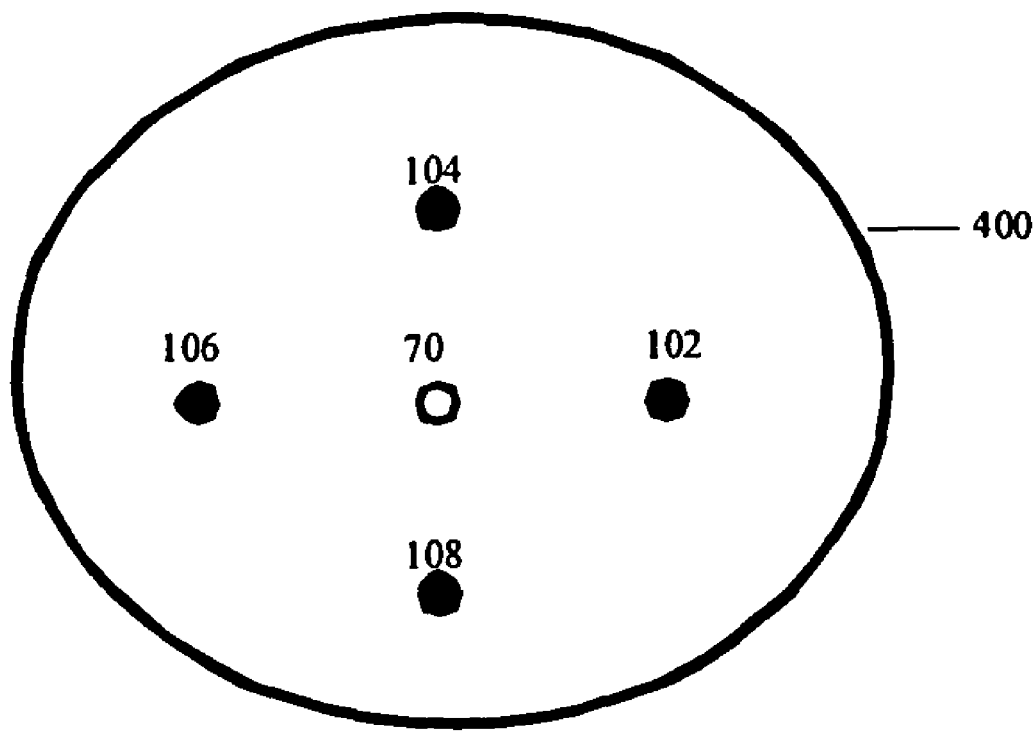
FIG. 6 is a schematic diagram showing a configuration of a 5-fiber skin-contact sensor consisting of one illumination fiber and four collection fibers.

FIG. 6 illustrates an end face 400 of the skin-contact sensor 200: the second light guide 80 contains four (4) optical fibers having four (4) distal ends 102, 104, 106, and 108 spaced around the distal end 70 of the first light guide 50. In this configuration, the proximal ends of the multiple light collection fibers are severally connected to multiple detectors. The fiber core diameter and the distances between the distal ends 102, 104, 106, and 108 of the collection light guide 80 and the distal end 70 of the illumination light guide 50 have insignificant effect on the performance of the infiltration sensor. Small-diameter fibers and short distances between various distal ends of the light guides allow the fabrication of smaller skin-contact sensor 200 that covers smaller sensing areas, allowing easier examination of the IV infusion site. A larger skin-contact sensor 200 facilitates easier attachment of the skin-contact sensor 200 to the skin. In another embodiment of the invention, the second light guide 80 is a single optical fiber and the first light guide 50 comprises multiple optical fibers having multiple distal ends spaced around the distal end 100 of the second light guide 80. In this configuration, the illumination light guide provides more evenly distributed electromagnetic radiation to the infusion site. In yet another embodiment of the invention, both the illumination and collection light guides 50 and 80 contain multiple optical fibers.

Figure 7:
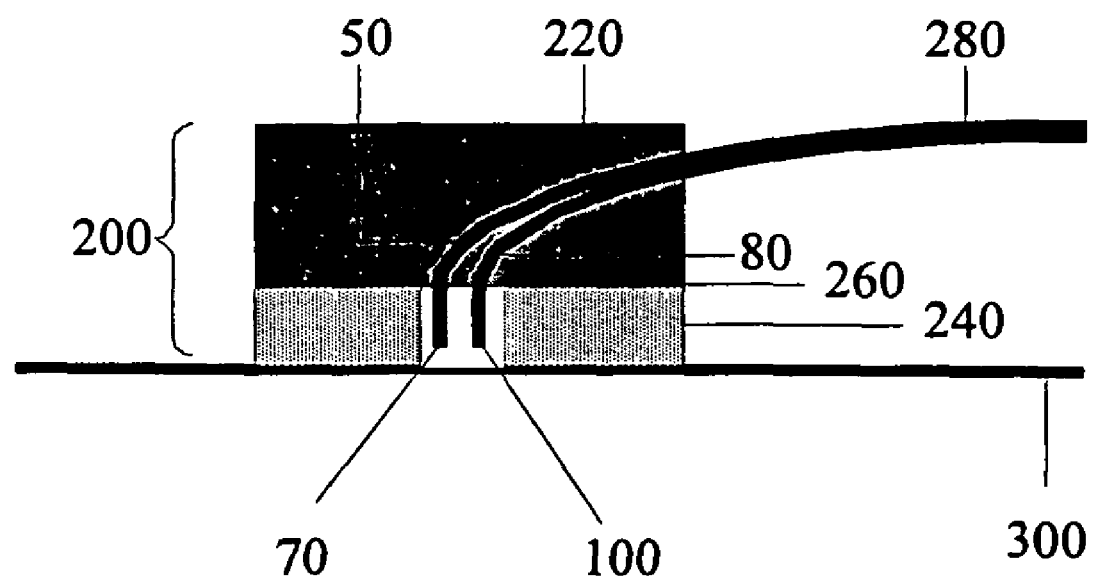
FIG. 7 is a schematic diagram showing a side view of the skin-contact sensor.

In one embodiment of the invention, the distal ends 70 and 100 of the illumination and collection light guides 50 and 80, respectively, are embedded in the skin-contact sensor 200 and are flush with the skin-contact side of the sensor. The skin-contact sensor 200 can be made of different materials, and in the present invention, both wood and plastics are used. The distance between the distal ends 70 and 100 is a few millimeters. In another embodiment of the invention, the ends of the illumination and collection light guides 50 and 80, respectively, are embedded in a wood or plastic base plate 220 which is secured to a foam pad 240 using an adhesive such as epoxy 260, as shown in FIG. 7. The foam pad 240 has an opening in the center that provides optical access to the skin 300. In this configuration, the skin-contact sensor 200 consists of a base plate 220, a foam pad 240, the interfacing medium, epoxy, 260, and the distal ends 70 and 100 of the light guides 50 and 80. In the present embodiment of the invention, the base plate 220 and the foam pad 240 have about the same lengths and widths, whereas the thickness of the foam pad 240 (~2-3 mm) is smaller than that of the base plate 220 (~5-10 mm), and the distal ends 70 and 100 of the light guides 50 and 80, respectively, extend beyond the epoxy interface between the base plate 220 and the foam pad 240. In this configuration, the effects of ambient light on the collected signals may be reduced, since the foam pad, when secured with a securing medium such as surgical tapes to the skin 300, may provide better light shields than a rigid skin-contact sensor 200 made of wood or plastic, as described previously.

In a preferred embodiment of the invention, referring to FIG. 7, the illumination light guide 50 and the collection light guide 80 are threaded through a 20-gauge black polyvinyl chloride (PVC) tubing 280 to reduce ambient light. The PVC tubing 280 that contains light guides 50 and 80 is secured to the base plate 220 with a securing medium such as epoxy. The distance between the distal ends 70 and 100 is about a few millimeters.

Figure 8:
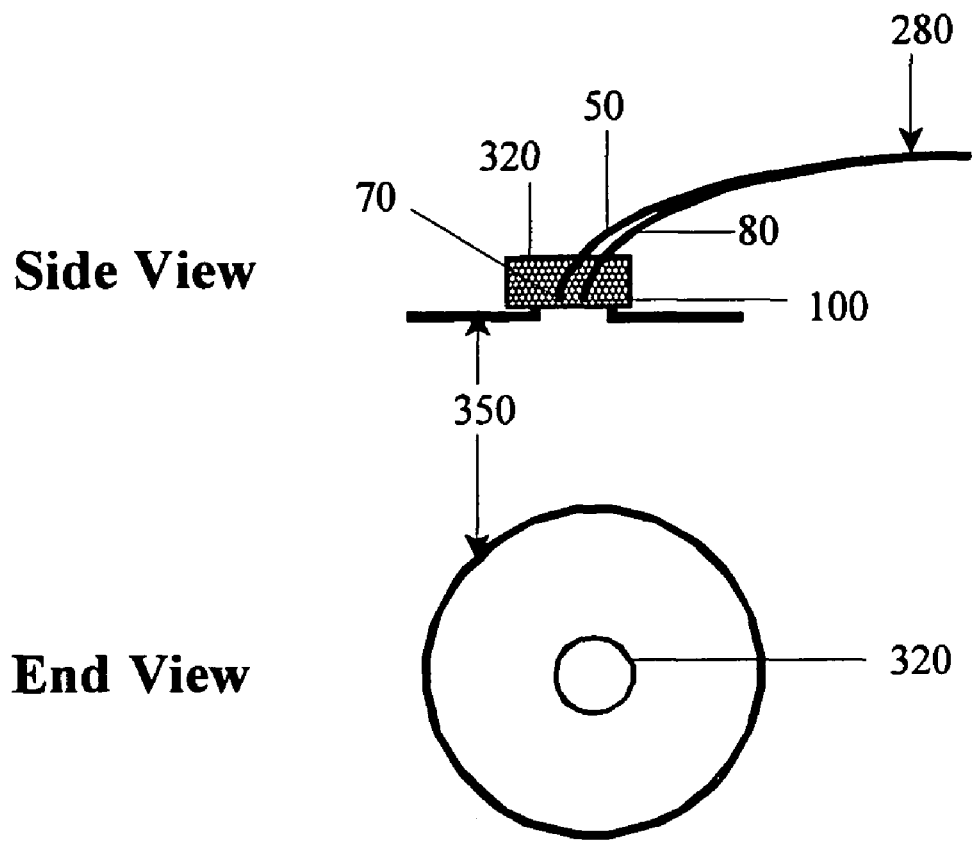
FIG. 8 is a schematic diagram showing the side and end views of the flanged skin-contact sensor.

In yet another embodiment of the invention shown in FIG. 8, the distal ends 70 and 100 of the first and second light guides 50 and 80, respectively, are embedded in an adaptor 320 that can be secured via a locking mechanism to an adaptor such as a flange 350, and the flange 350 is secured to the skin 300 near the infusion site via a securing mechanism. The flange can be of any shape that is compatible with the skin-contact sensor 200. FIG. 8 shows one example of the end view of a circular-shaped flange. The flange 350 can be made of biocompatible materials that are acceptable for use in clinical settings; it can be either disposable or reusable. Use of an adaptor may reduce the effect of motion artifacts and provide strain relief from the IV line.

Figure 9:
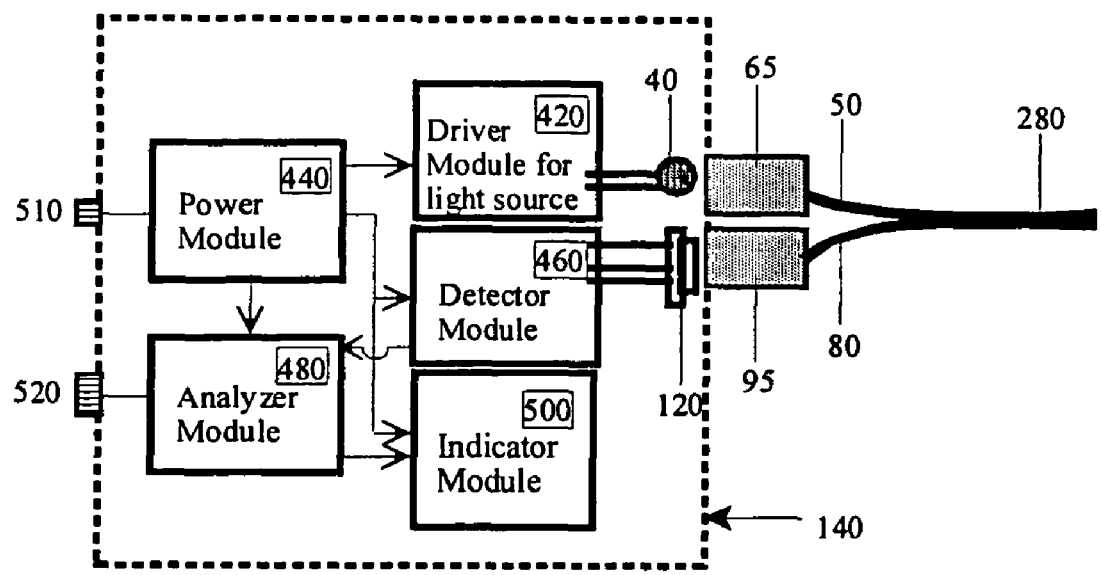
FIG. 9 is a schematic block diagram showing the electronics unit of the optical infiltration detection apparatus.

FIG. 9 shows the schematic diagram of the electronics unit 140 of the IV infiltration detection apparatus. In one embodiment of the invention, the proximal ends 60 and 90 of the illumination and collection light guides 50 and 80, respectively, are connected to the electronics unit 140 via SMA connectors, 65 and 95, respectively. The electronics unit 140 consists of a driver module 420, a power module 440, a detector module 460, an analyzer module 480, and an indicator module 500. The driver module 420 controls the light source 40, providing a stable illumination to the sensing site on the skin. The power module 440 controls input power to the driver module 420, detector module 460, analyzer module 480, and indicator module 500. In the present invention, a light source such as an LED is enclosed in the electronics unit 140 which has an internally adjustable gain mounted on a circuit board for controlling the voltage applied to the LED. For alignment purposes, the LED can also be controlled manually. The detector module 460 consists of an amplifier with adjustable gain and offset. It receives signals from the photodetector 120 and sends the signals to the analyzer module 480. In one embodiment of the invention, a band pass filter centered at 850 nm is mounted in front of the photodetector to increase the signal to noise ratio (SNR). In an alternate embodiment of the invention, a long-pass filter with a cut-on wavelength of around 850 nm is used. The analyzer module 480 stores and analyzes the signals received from the detector module 460 and sends the analyzed signals to the indicator module 500. The indicator module 500 triggers an alarm signal when the analyzed results reach a pre-selected level; it also comprises an optional shut-off feature allowing the interruption of the flow of IV fluid upon the detection of IV infiltration. In an advanced embodiment of the invention, the electronics unit 140 can be a circuit board incorporated into an infusion pump or a standalone monitor.

Referring to FIG. 9, in one embodiment of the invention, the electronics unit 140 is powered either by a 9-volt DC battery contained in the unit or an AC source. When using the AC source, an AC-to-DC converter is required to convert the AC power to DC and the DC power is delivered to the electronics unit 140 through a DC port 510. The power module 440 provides 5-volt DC to the LED 40 and 12-volt DC to the detector module 460. The driver module 420 contains a voltage divider circuitry for adjusting the voltage across the LED 40 to control its intensity. The electronics unit 140 integrates the collected signals and stores the integrated data. A computer equipped with a data acquisition board with a sampling rate of 40 kHz is interfaced to the electronics unit 140 through the communication port 520 for programming the microprocessor inside the electronics unit 140, receiving data from the microprocessor, and transferring the data to a disk file or other storage devices such as memory chips and/or flash cards. The microprocessor performs limited functions such as data collection, integration, setting the alarm threshold, setting the detector gain, and initiation of the measurement. In the present invention, specially designed and developed software programs are used to control the operating parameters.

While the invention has been described with reference to specific embodiments, modifications and variations of the invention may be constructed without departing from the scope of the invention, which is defined in the following claims.

The invention claimed is:

1. Intravenous infiltration detection apparatus comprising:
   an electronic unit
   a power supply connected to the electronic unit,
   a continuous single wavelength single light source connected to the power supply for delivering non-encoded light in a certain spectral range,
   a first disposable light guide comprising an optical fiber having proximal and distal ends, the proximal end being optically connected to the light source for conducting light from the light source, the distal end being configured for mounting near an IV infusion site of a patient,
   a second disposable light guide comprising an optical fiber having proximal and distal ends, the distal end being configured for mounting near the infusion site for receiving the electromagnetic radiation reflected, scattered, diffused or otherwise emitted from the patient's tissue near an intravenous needle injection site,
   a detector in the electronics unit at the proximal end of the second light guide for detecting light from the guide,
   an analyzer in the electronics unit connected to the detector for analyzing the received light, wherein analyzing further comprises comparing intensity of the received light,
   an indicator connected to the analyzer in the electronics unit for providing information on the occurrence of infiltrations, and
   a disposable skin contact sensor fixed to and holding the distal ends of the first and second light guides against the patient's tissue.

2. The apparatus of claim 1, wherein the electronics unit is configured to compensate both a baseline light signal value and the light signal during infusion with an ambient light signal value.

3. The apparatus of claim 1, wherein the electronics unit is configured to determine infiltration based on a ratio of a baseline light signal value compensated with an ambient light signal value and the light signal during infusion compensated with the ambient light signal value.

4. The apparatus of claim 1, wherein the distal end of the first light guide is modified for placement on the tissue of a patient.

5. The apparatus of claim 4, wherein the distal end of the second light guide is modified for placement on the tissue of a patient.

6. The apparatus of claim 5, wherein the distal ends of the first and second light guides comprise a skin contact sensor and an adhesive base for attaching the contact sensor to the skin.

7. The apparatus of claim 5, wherein the first and second light guides comprise optical fibers, and wherein the first light guide comprises multiple light-illuminating optical fibers having proximal ends connected to the non-encoded light source of a certain spectral range.

8. The apparatus of claim 5, wherein the first and second light guides comprise optical fibers, and wherein the second light guide comprises multiple light-receiving optical fibers having proximal ends severally connected to a photon detection device.

9. The apparatus of claim 5, wherein the first and second light guides comprise optical fibers, and wherein both light guides comprise multiple optical fibers having proximal ends of the first light guide connected to the non-encoded light source of a certain spectral range and proximal ends of the second light guide connected to the photon detection device.

10. The apparatus of claim 9, wherein the distal ends of both light guides are placed near the intravenous needle injection site.

11. The apparatus of claim 1, wherein the light source is a near-infrared or red light emitting diode.

12. The apparatus of claim 1, wherein the electronics unit comprises an analyzer module, a power module, the non-encoded light source, a driver module, a detector module, and an indicator module.

13. The apparatus of claim 12, wherein the analyzer module comprises a microprocessor for digitizing, processing, analyzing, and storing signals.

14. The apparatus of claim 12, wherein the indicator module comprises an alarm circuitry and wherein the alarm is selected from the group consisting of an optical alarm, an audible alarm, an analog alarm, a digital alarm, a computerized alarm, a mechanical alarm, and an analog or digital signal pre-connected to a remote alarm.

15. The apparatus of claim 12, wherein the light source comprises an LED.

16. The apparatus of claim 12, wherein the driver module comprises a voltage circuitry for energizing and de-energizing the light source, and for regulating the light source intensity.

17. The apparatus of claim 12, further comprises a computer having a data acquisition board connected to the electronics unit for comparing pre-infusion signals with during-infusion signals.

18. The apparatus of claim 1, wherein attaching the distal ends of both light guides to skin comprises a circular sleeve secured to the tissue of a patient.

19. A method of monitoring tissue infiltration during IV infusion, comprising:
    directing non-encoded continuous single wavelength light in a certain spectral range from a single light source through a first disposable light guide fixed in a disposable sensor on the patient's tissue into the patient's tissue near an IV site,
    collecting light reflected, scattered, diffused or otherwise emitted from the patient's tissue,
    transmitting the light emitted from the patient's tissue through a second disposable light guide fixed in the disposable sensor,
    receiving the collected light from the tissue before and during IV infusion,
    comparing intensity of light received before and during infusion, and
    providing an alarm indicative of tissue infiltration upon a preselected level of differences in the collected light received at the present time and a baseline, wherein receiving the collected light comprises receiving the collected light from areas near the directed light.

20. The method of claim 19, wherein comparing comprises comparing a ratio of the light received before infusion compensated with an ambient light signal value and the light received during infusion compensated with the ambient light signal value to a preselected level.

21. Intravenous infiltration detection method comprising:
    providing a power supply,
    connecting a non-encoded continuous single wavelength single light source to the power supply,
    providing a first light guide with proximal and distal ends, optically connecting the proximal end to the light source for conducting light from the light source, attaching the distal end to a skin-contact sensor, mounting the skin-contact sensor to the tissue near an IV infusion site,
    providing a second light guide with proximal and distal ends, configuring the distal end of the second light guide for mounting near the tissue of the patient near the IV infusion site for receiving the light reflected, scattered, diffused or otherwise emitted from the tissue,
    providing a detector at the proximal end of the second light guide,
    detecting light from the second light guide at the detector,
    providing an analyzer, comparing intensity of the received light,
    digitizing, analyzing, and storing signals from the detector at the analyzer,
    providing an indicator,
    indicating a preselected level of changes in the intensity of light signals collected pre-infusion and during infusion, and
    providing an alarm for alerting the patient or caregivers of potential infiltrations.

22. The method of claim 21, wherein indicating a preselected level of changes comprises indicating significant changes in a ratio of a pre-infusion light signal compensated by an ambient light value signal and an infusion light signal value compensated by the ambient light value signal.

23. The method of claim 21, further comprising placing the distal end of the first light guide on skin of the patient.

24. The method of claim 23, further comprising placing the distal end of the second light guide on skin of the patient.

25. The method of claim 24, further comprising mounting the distal ends of the first and second light guides in a skin-contact sensor for attachment to the skin.

26. The method of claim 25, wherein the providing of the first and second light guides comprises providing optical fibers.

27. The method of claim 21, wherein providing the light source comprises providing a light-emitting diode.

28. The method of claim 21, wherein providing the electronics unit comprises providing an analyzer module, a power module, a light source driver module, a detector module, and an indicator module.

29. The method of claim 28, wherein providing the analyzer module comprises providing a microprocessor for digitizing, processing, analyzing, and storing signals.

30. The method of claim 28, wherein providing the indicator module comprising providing an alarm circuitry and wherein the alarm is selected from the group consisting of an optical alarm, audible alarm, an analog alarm, a digital alarm, a computerized alarm, a mechanical alarm, and an analog or digital signal pre-connected to a remote alarm.

31. The method of claim 28, wherein providing the light source comprises an LED.

32. The method of claim 28, wherein providing the driver module comprises providing a voltage circuitry for energizing and de-energizing the light source, and for regulating the light source intensity.

33. The method of claim 28, further comprises providing a computer having a data acquisition board connected to the electronics unit for comparing pre-infusion signals with during-infusion signals.

34. The method of claim 21, wherein attaching the distal ends of both light guides to skin comprises a circular sleeve secured to the distal ends and secured to the tissue of the patient.

* * * * *